United States Patent
Gilson et al.

(10) Patent No.: US 8,512,373 B2
(45) Date of Patent: Aug. 20, 2013

(54) SUTURE DEVICE

(75) Inventors: Paul Gilson, Uggool Moycullen (IE);
Geoffrey H. White, Birchgrove (AU);
Jassim Daood, Darling Point (AU)

(73) Assignee: Aesthetic Devices Pty Limited, Crows Nest (AU)

( * ) Notice: Subject to any disclaimer, the term of this patent is extended or adjusted under 35 U.S.C. 154(b) by 18 days.

(21) Appl. No.: 13/128,552

(22) PCT Filed: Nov. 13, 2009

(86) PCT No.: PCT/AU2009/001474
§ 371 (c)(1),
(2), (4) Date: Jul. 26, 2011

(87) PCT Pub. No.: WO2010/054431
PCT Pub. Date: May 20, 2010

(65) Prior Publication Data
US 2011/0282385 A1    Nov. 17, 2011

(30) Foreign Application Priority Data
Nov. 13, 2008   (AU) ................................ 2008905871

(51) Int. Cl.
*A61B 17/06*    (2006.01)

(52) U.S. Cl.
USPC .......................................................... 606/224

(58) Field of Classification Search
USPC .......... 606/224, 228, 139–145, 185; 604/264
See application file for complete search history.

(56) References Cited

U.S. PATENT DOCUMENTS

| | | | | |
|---|---|---|---|---|
| 2,814,296 | A * | 11/1957 | Everett | 604/265 |
| 4,946,467 | A * | 8/1990 | Ohi et al. | 606/228 |
| 5,865,836 | A * | 2/1999 | Miller | 606/228 |
| 2005/0256535 | A1* | 11/2005 | Capurro | 606/185 |
| 2006/0025819 | A1* | 2/2006 | Nobis et al. | 606/232 |
| 2008/0108957 | A1* | 5/2008 | Cumbo | 604/264 |
| 2009/0030453 | A1* | 1/2009 | Daood | 606/223 |

FOREIGN PATENT DOCUMENTS
WO    2007098535    9/2007

* cited by examiner

*Primary Examiner* — Corrine M McDermott
*Assistant Examiner* — Christina Lauer
(74) *Attorney, Agent, or Firm* — Michael B. Rubin; Bozicevic, Field & Francis LLP (57) ABSTRACT

A needle assembly comprises a shaft with two opposite tissue piercing ends. The assembly includes a shuttle which is moveable relative to the shaft between the two ends. The shuttle comprises means to secure a suture to the shuttle member.

27 Claims, 9 Drawing Sheets

SUTURE DEVICE

FIELD OF THE INVENTION

The present invention relates to needles and particularly to medical suture needle assemblies.

BACKGROUND ART

Many types of needles are available for a variety of surgical indications, ranging from simple closure of surface wounds to complex anastomoses and repair of various tissues.

In a most basic form, sutures are attached to a needle through an eye located at one end. Following puncture through the skin and tying of an end, the needle travels subcutaneously to an exit point whereupon both the needle and trailing suture are pulled through the skin. The suture is tied at the exit point and the steps repeated as required. The result of such suturing is substantial scarring which is, at the least, cosmetically undesirable.

In WO2007/098535, a double tipped needle with an elongate lumen is disclosed. The suture attached to this needle moves along the elongate lumen to enable a surgeon to manipulate the needle to retain a suture subcutaneously. With only the tips of the needle forming small puncture wounds scarring is greatly reduced.

There is still a need for a needle assembly which provides a means to effectively tunnel a suture subcutaneously and which has structural integrity and allows for more precision in controlling the orientation and depth of a suture beneath the skin.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In a first aspect, the present invention consists in a needle assembly comprising:
 an elongate shaft having a first tissue piercing end and a second tissue piercing end;
 a shuttle member moveable relative to said elongate shaft between said first and second tissue piercing ends;
 said shuttle member comprising at least one suture securing means to secure a suture to the shuttle member.

According to a second aspect, the present invention is a method of subcutaneously positioning at least one suture in an individual, comprising:
 (a) providing a needle assembly comprising an elongate shaft having a first tissue piercing end and a second tissue piercing end;
 a shuttle member moveable relative to said elongate shaft between said first and second tissue piercing ends;
 said shuttle member comprising at least one suture securing means which secures said at least one suture to the shuttle member;
 (b) subcutaneously introducing the at least one suture by passing the first tissue piercing end of the elongate shaft into and under the skin of the individual;
 (c) moving said elongate shaft relative to the skin such that said first tissue piercing end exits the skin at first exit site, remote from the position at which it entered and wherein the second tissue piercing end, the shuttle member and at least a portion of the at least one suture is retained beneath the surface of the skin; and
 (d) passing the second tissue piercing end of the elongate shaft subcutaneously and causing it to exit the skin at a second exit site, remote from the first exit site; and wherein the first tissue piercing end and at least a portion of the at least one suture is retained beneath the surface of the skin.

In one embodiment said method includes repeating steps (c) and (d) to further subcutaneously advance the at least one suture.

By the term "suture", it is to be understood that the scope of this invention covers various forms of suture including tape, thread or cord. The suture may be made from an absorbable material such that it is resorbed in situ. Alternatively, the suture may be made from a non-resorbable material. In one embodiment, the suture may be made from a metallic material. The suture may further be made from an elastomeric material as discussed further herein. The suture may be made from a combination of materials.

The shuttle member is preferably longitudinally moveable along at least a length of said elongate shaft. The shuttle member may also be rotationally moveable relative to the shaft. In a preferred embodiment said shuttle member is fully rotatable relative to the shaft.

The shuttle member may be positioned within the shaft. The shuttle member may, alternatively, be positioned at least partially within the shaft. In these embodiments, at least part of the shaft is tubular, with an internal lumen to receive at least part of the shuttle.

Preferably, the shuttle member is positioned external to the shaft. In this embodiment, the shaft is preferably a solid member. The shuttle member may comprise a substantially tubular body extending from a proximal end to a distal end and having an inner wall defining a lumen to receive at least part of the shaft. The entire inner wall of the shuttle member may interface with the external surface of the shaft. The interface between the shuttle member and the shaft is such that the shuttle is longitudinally moveable along a length of the shaft.

The cross-section of the shaft may be circular. In a further embodiment the cross section of the shaft may be non-circular. The cross section of the shaft may be oval or elliptical, or flattened or triangular.

There may be some degree of friction between the shuttle member and the elongate shaft irrespective of whether the shuttle is internal or external the shaft. This friction does not prevent said longitudinal movement of the shuttle member relative to the elongate shaft.

The degree of friction between the shuttle member and the elongate shaft may vary and in one embodiment, the friction may vary along the length of the elongate shaft. In this embodiment, there may be an area of increased friction between said two components to cause the shuttle to slow and in some embodiments stop.

In the embodiment of the invention wherein the shuttle member is external the elongate shaft, the increase in friction may be realised by an increase in diameter of the elongate shaft to bring the shuttle member and elongate shaft into relatively tight frictional engagement. In another embodiment, the friction may be increased by providing a different material and/or surface features of the elongate shaft at or in a region along its length. Preferably, the elongate shaft would have at least two areas of increased frictional engagement with the shuttle member. Said areas of increased friction may be substantially adjacent to the first and second tissue piercing ends so as to prevent the shuttle member from travelling beyond said ends.

The needle assembly may also comprise at least one stop member on said elongate shaft. Preferably, the assembly includes at least two stop members relatively spaced on the outer surface of the shaft. The stop members stop the longitudinal travel of the shuttle and so are preferably positioned adjacent to the first and second tissue piercing tips respectively. In another embodiment, the stop members may be more closely spaced to one another to limit the longitudinal movement of the shuttle.

The stop members typically comprise ramp-like structures. In this embodiment, the proximal or distal ends of the shuttle ride up the ramp until the shuttle is prevented from moving further in a longitudinal direction. When the shaft is moved in a different direction, the shuttle slides back down the ramp and travels longitudinally along said shaft. The ramp-like structure aids in preventing "sticking" of the shuttle on the stop member.

In one embodiment, only the inner wall at or adjacent to the distal end and/or the proximal end of the shuttle engages the external surface of the shaft.

The inner wall and/or outer wall of the shuttle member may be substantially straight along a longitudinal axis. Alternatively, the inner and/or outer walls may curve between the proximal and distal ends thereof. The inner wall and/or outer wall may curve convexly or concavely between said proximal and distal ends. Typically, the shuttle member comprises an inner concavely curving wall and an outer convexly curving wall. Alternatively, the inner wall may be substantially straight and the outer wall convex. The outer wall may be substantially straight and the inner wall concave.

The diameter of the shuttle member at its widest point is preferably less than or equal to the diameter of the widest part of the elongate shaft.

Preferably, the outer surface of the shuttle member is relatively smooth with no sharp edges or angles. At the proximal end of the shuttle member, the inner and outer surfaces of the shuttle are spaced by a leading end face. In this embodiment, both the inner and outer surfaces may taper at a joining region between the inner and outer surface and the leading end face. The leading end face may be substantially planar. Alternatively, the leading end face may comprise a substantially domed surface.

Similarly, the distal end may comprise a trailing end face wherein the inner and outer surfaces taper at a joining region between the internal and outer surface and the trailing end face. The trailing end face may be substantially planar. Alternatively, the trailing end face may comprise a substantially domed surface.

The shuttle member of the invention is typically manufactured as one piece. The shuttle member may be made from any suitable biocompatible material. Preferably it is made from a metal or a metal alloy including stainless steel, nickel, aluminium, titanium, zirconium, niobium, molybdenum, silver, indium, hafnium, tantalum, tungsten, iridium, platinum and gold, copper or alloys of said elements. Alternatively, the shuttle member may be made from a non-metallic material including one or more biocompatible polymers or ceramics.

The shuttle member may further comprise a coating. The coating may include a lubricious coating. Examples of suitable coatings include silicones or polytetrafluoroethylene (PTFE).

In embodiments wherein the shuttle member is made from a non-radiopaque material, it may include radiopaque markers to allow visualisation by a surgeon during a surgical procedure.

The suture securing means of the shuttle may comprise at least one aperture in the shuttle. The aperture may extend from a first opening defined by the outer wall to a second opening defined by the inner wall. The suture securing means may further comprise a fixing member to fix a suture in said at least one aperture. A plurality of sutures may be secured to the shuttle member.

Alternatively, the suture securing means may comprise at least two apertures in the shuttle. In this embodiment, both of said apertures extend from respective first openings defined by the outer wall to respective second openings defined by the inner wall. Said at least two apertures may be located relatively adjacent to each other along substantially the same longitudinal axis of the shuttle member. Similarly, the two apertures may be positioned relatively adjacent to each other along substantially the same lateral axis.

A leading length of the suture may be threaded through one of said apertures and out of the other aperture to secure it to the shuttle member. The leading length of the suture may be secured to a trailing length of the suture by, for example, tying, crimping, adhesive, clipping or other such means. The result is a closed loop of suture secured to the shuttle member via said apertures.

The suture securing means may further comprise a tethering member. The tethering member may be spaced from said shuttle member and may tether the suture to the shuttle member. In one embodiment, a leading length of a suture is threaded through the one aperture and out another aperture in the shuttle. The leading length is tethered to a trailing length of the suture by said tethering member.

The tethering member typically comprises a tubular body having an inner lumen to receive a length of suture. The inner lumen is typically substantially straight. The outer surface of the tethering member may be straight or curved. Wherein the outer surface is curved, it may be curved either convexly or concavely. In the latter configuration, the tethering member may comprise a dumbbell structure with first and second end regions of the tubular body having a greater thickness than a relatively thinner central crimping region.

The tethering member is typically made from a biocompatible material and typically a biocompatible metal or alloy. Preferably, the material is substantially malleable to allow the tethering member to be readily crimped around the suture. Examples of suitable materials include stainless steel, nickel, aluminium, titanium, zirconium, niobium, molybdenum, silver, indium, hafnium, tantalum, tungsten, iridium, platinum and gold, copper or alloys of said elements. Alternatively, the tethering member may be made from a non-metallic material including one or more biocompatible polymers. In this embodiment, said biocompatible polymer may include radiopaque markers thereon or therein.

If using a metallic or other tethering member with radiopaque markers, a user may visualise the tethering member thus enabling precise control during a suturing procedure.

The shuttle member may be joined to the suture or tether by way of a universal joint. In one embodiment the joint may include a ball and socket joint. Alternatively, the joint may include a hinge arrangement. The universal joint may facilitate the change in direction of the shuttle member during use.

The angle of the suture relative to the shuttle member may differ in different embodiments of the invention. For example, the suture or plurality of sutures may extend substantially perpendicular relative to the shuttle member. In a further embodiment, the suture or plurality of sutures may extend substantially parallel to the shuttle member. The suture(s) may also extend at an angle anywhere in the range between said substantially perpendicular and substantially parallel configurations.

In an embodiment wherein the assembly includes a plurality of sutures, the angle of each suture relative to the shuttle may vary in relation to one another.

The tissue piercing ends of the elongate shaft may comprise a number of different types of tips. An example of a suitable tip is a trocar tip. Alternatively the tip may be a diamond tip.

The elongate shaft is preferably made from a suitable biocompatible material including metals and metal alloys or a combination thereof. In one embodiment, the elongate shaft is made from stainless steel. The stainless steel may include surgical grades 316 or 420. Further, the elongate shaft may be made from a suitable polymeric material. In another embodiment, the elongate shaft may be made from a combination of materials. One example is a combination of a suitable metal and a polymeric material.

The shaft may also comprise depth markers at intervals along it length.

The elongate shaft and/or the shuttle and/or the tethering member are typically machine polished post manufacture such that the surfaces are free from scratches and burrs. One or more component may also be coated with a lubricious coating. Examples of suitable coating materials include silicones and polytetrafluoroethylene (PTFE).

The needle assembly allows one or more sutures to be positioned subcutaneously and to remain in a subcutaneous position as they are tunneled through surrounding tissue. At any given time during the procedure, one of the ends of the elongate shaft is beneath the skin thus retaining the suture(s) beneath the skin. By pivoting the elongate shaft, the shuttle member shifts longitudinally along the elongate shaft, with the suture tethered thereto.

The elongate shaft may be manipulated during a procedure to change the direction of the skin piercing end that is positioned subcutaneously. For example, as the first skin piercing end exits the skin, the shaft may be pivoted such that the trailing second skin piercing end is moved from a relatively rearward facing direction to a relatively forward facing direction subcutaneously. Pressure may then be applied to the needle to cause what was the trailing second end to pass subcutaneously and to exit the skin at a position remote from an entry point.

An advantage of the present needle assembly is that it enables the positioning of a suture(s) beneath the skin over a range of lengths without the requirement for individual incisions to position the suture(s). The only marks left on the patient are the elongate shaft entry and exit points which are far less likely to leave scarring.

The needle assembly of the present invention may be for single-use or multi-use.

The needle assembly may have applications in a number of surgical procedures where suturing is required. In one embodiment, the assembly may be used in a cosmetic surgery application. Examples of suitable procedures include face lift surgery. In a further embodiment the needle assembly may be used to perform breast lift surgery.

Alternatively the assembly may be utilised in a buttock lift procedure. Other indications include brow lift, thigh lift; tummy tuck or arm lift surgery.

In a further aspect, the present invention provides a needle assembly comprising:
  an elongate shaft having a first tissue piercing end and a second tissue piercing end;
  a shuttle member moveable relative to said elongate shaft between said first and second tissue piercing ends; and
  a suture connected to the shuttle member.

The suture thread used with the needle assembly of the present invention may comprise an elastomeric structure. The entire suture thread may be made from an elastomeric material. Alternatively the thread may have an elastomeric core which is overlayed by a sheath. The sheath may have less elasticity than the core. Alternatively the sheath may have greater elasticity than the core.

The entire thread may be made from a suitable biocompatible material. In embodiments comprising a core and a sheath, the sheath may be made from a suitable biocompatible material. Alternatively, the sheath may also be made from an elastomeric material, different to the elastomeric material of the core. For example, in this embodiment, while still having elastomeric properties, the sheath may not be stretched to the same extent as the core. It is preferable however, that the sheath or other interface with the body is made from a relatively biocompatible material, The elastomeric material of the suture thread may be a polymeric-based material. Examples of suitable materials include silicone rubber. In further embodiments, the elastomeric material may comprise purified natural rubber, isoprene cisobutylene, abrylonitrile butadiene copolymer or derivatives.

The sheath of the suture thread may include polytetrafluoroethylene (PTFE), polyvinylidine fluoride, polypropylene, polyurethane-polyether, collagen, polyglyconate or derivatives. Natural fibres which may be used include silk, collagen, cotton and linen.

The sheath may be helically wound around the core. Alternatively, the sheath may be interwoven to form a mesh structure around the core. Further, the sheath may be molded with the core to form a unitary structure.

The suture thread may further comprise pharmacological substances within its structure for release into the surrounding tissue when implanted in a subject. For example, the thread may include or be coated with anti-inflammatory agents or antibiotics. In still further embodiments, the thread may include agents to enhance tissue ingrowth. The thread may further be coated with agents to improve lubricity, including silicone or polytetrafluoroethylene (PTFE).

The elastomeric suture thread may be substantially circular in cross-section. Alternatively the suture thread may be relatively flattened. In one embodiment the cross-section could be oval or elliptical in cross-section.

The elastic properties of the abovementioned suture thread typically assists in a surgical procedure such as the cosmetic procedures outlined. For example, in a breast lift procedure the suture thread may be positioned using the assembly of the present invention such that it forms a lasoo type arrangement to lift the base of the breast upwardly. The elastomeric nature of the thread substantially prevents any trauma to the tissue during the lift and also provides for a more natural look of the breast post surgery. Particularly, the elastomeric nature of the suture thread allows a degree of stretch of the thread as the breast moves. Such an advantage enables a patient to enjoy a fuller life and to include activities such as running which would not be so comfortable with a non-stretch suture.

The suture thread may have constant elasticity along its length. Alternatively the elasticity may be variable along its length. At least one region of the suture thread may have greater elasticity than other regions to provide such variability.

Preferably, the suture thread is capable of stretching by up to 100% of its length. In other embodiments, the suture thread is capable of stretching by up to 75% of its length, or up to 50% of its length or up to 25% of its length. In one embodiment, the suture thread may stretch by between 5% and 25% of its length.

The suture thread, whether having elastic properties or not, may also include one or more barbs along its length. The barbs may lodge in the tissue and enhance a surgical procedure such as the cosmetic procedures discussed above. The barbs are preferably molded on the thread such that the risk of dislodgement in situ is minimised.

The barbed suture may be configured as a single-ended suture with a plurality of barbs aligned to allow the suture to move through tissue in one direction and to resist moving through the tissue in the other direction. The barbed suture may also comprise a double-ended suture wherein the barbs on a first end portion are arranged to facilitate the suture to move through tissue in a first direction and the barbs on a second end portion are aligned to allow the suture to move through tissue in a second different direction.

The barbs may be closely spaced along the suture body for situations where a high gripping force is needed. Alternatively they may be spaced apart for applications where less gripping is required.

The barbs may include one or more extension legs. The legs of each barb may be oriented in the same direction along the length of the thread. The legs may be substantially straight or may have a curved surface to allow the suture thread to smoothly pass through tissue.

The barbs may be integrally molded with the suture thread. Alternatively the barbs may be attached to the thread. In this embodiment, the barbs may be provided separately and attached by a surgeon as required. It is envisaged that the barbs could be slid over the suture thread or attached by other means including crimping. The barbs may be made from the same or a different material to the suture thread.

The barbs may further act to join a plurality of sutures together. In this embodiment, the sutures may be held together to form a net-like structure.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

DETAILED DESCRIPTION OF AN EXEMPLARY EMBODIMENT OF THE INVENTION

The needle assembly 10 of the present invention includes an elongate shaft 11 and a shuttle 12. The shaft 11 has two tapered ends 11a and 11b which are designed to pierce tissue. Typically the ends 11a and 11b are trocar tips.

The shuttle 12 is longitudinally moveable along a length of the shaft 11 and comprises a securing means to secure a suture 18 to the shuttle 12.

The shuttle 12 in addition to being longitudinally moveable along a length of the elongate shaft 11 is also fully rotatable relative to said shaft 11.

In the embodiments depicted, the shuttle 12 is positioned outside the shaft 11. The shaft in the embodiments depicted in FIGS. 1 to 6 is a solid structure which provides a stiffer structure at any given diameter than a needle shaft with either an eye or having a slot to receive a shuttle 12.

Figure 3:
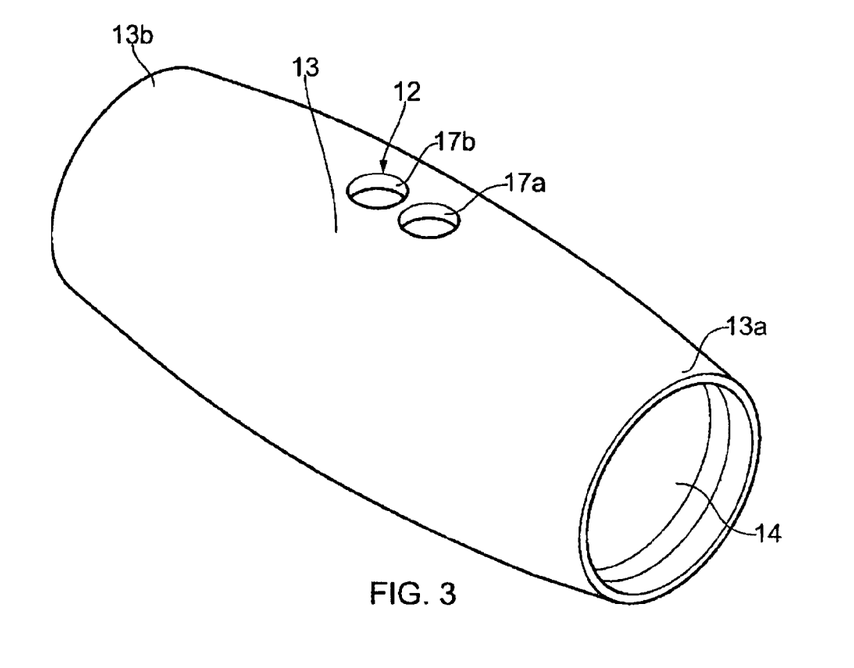
FIG. 3 is a side elevational view of a shuttle according to the present invention.
Figure 3A:
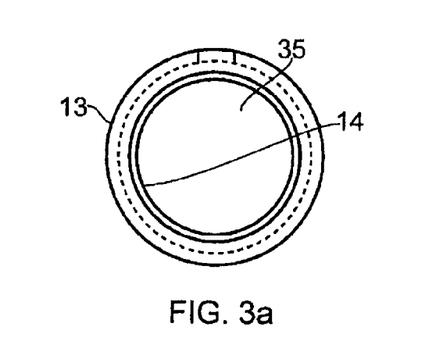
FIG. 3a is a cross-sectional view of the shuttle of FIG. 3.

The shuttle 12 is depicted in FIG. 3 as a substantially tubular body 13 extending from a proximal end 13a to a distal end 13b. An inner wall 14 defines a lumen 35 to receive the shaft 11 of the needle assembly 10. As mentioned above, there may be some degree of friction between the shuttle 12 and the shaft 11. The degree of friction between the shuttle 12 and the shaft 11 may vary along the length of the shaft 11. While variable, the friction must not be so great as to limit the movement of the shuttle along a substantial length of the shaft. The invention requires a relatively free longitudinal movement of the shuttle along the shaft to cause suture 18 to also follow the path of movement along the shaft. A relatively free rotation of the shuttle around the shaft is also desirable. This will become evident when describing a procedure below wherein rotation of the shuttle avoids the need to rotate the shaft to ensure that the suture 18 is trailing correctly.

However, the interface between shuttle and shaft may comprise a frictionally tight engagement at specific regions located towards first end 11a and second end 11b. Such tight friction regions typically at least slow the shuttle in its travel along the length of the shaft and may in fact stop the shuttle.

Figure 8:
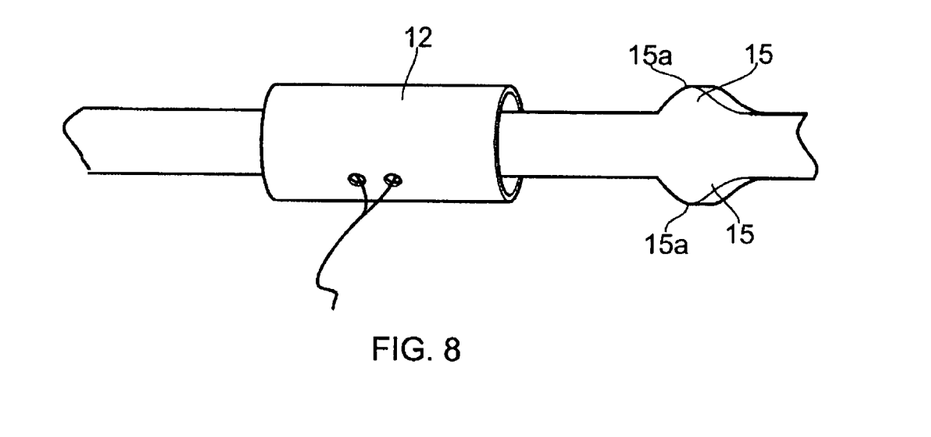
FIG. 8 depicts a further embodiment of the invention

To avoid the shuttle 12 sticking at any point along the shaft, it may be stopped by discrete stop members 15 as depicted in FIG. 8. The depicted stop member 15 comprise ramp members. The shuttle 12 rides up the ramp until it is prevented from moving further in a longitudinal direction due to the height of the highest point of the ramp 15a being greater than the diameter of the shuttle.

Figure 1:
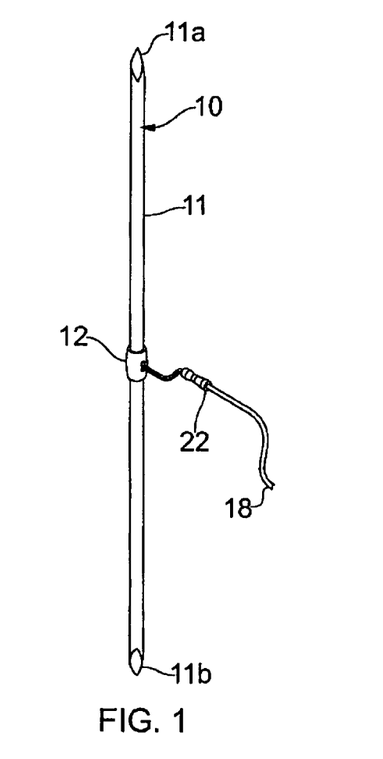
FIG. 1 is a schematic representation of the assembly of the present invention.
Figure 2:
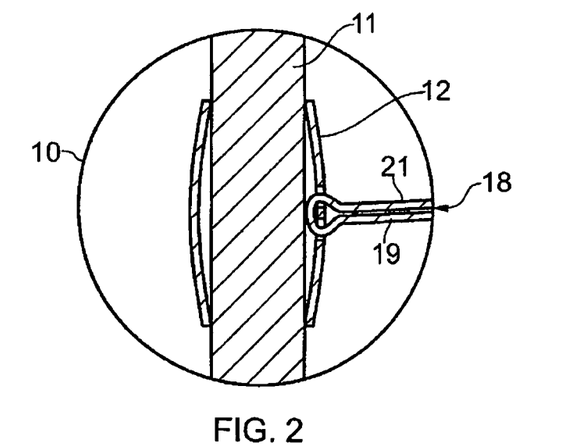
FIG. 2 is an exploded cross-sectional view of the shuttle component of the assembly of FIG. 1.

In the cross-sectional representation in FIG. 2, the shuttle is depicted as engaging the shaft 11 only at its proximal and distal ends 13a and 13b. This limits the degree of friction between the two components allowing the shuttle to move relatively freely along the length of the shaft 11.

The shuttle is shown as comprising a relatively curved tubular structure with both a curved inner wall 14 and a curved outer wall 16. The diameter of the shuttle at its greatest is desirably no greater than the widest diameter of shaft 11. Typically the widest diameter of the shaft 11 is a length of shaft before it tapers to the first and second ends 11a and 11b.

The smooth, curved outer surface of the shuttle prevents it nicking or cutting adjacent tissue as it shuttles along the shaft.

The suture securing means of the shuttle is depicted in FIG. 3 as two apertures 17a and 17b in the shuttle. Both the apertures extend from an opening defined by the outer wall 15 to a second opening defined by the inner wall 14.

The apertures are positioned adjacent to one another such that a suture 18 may be threaded therethrough as shown in detail in FIG. 2.

Figure 4A:
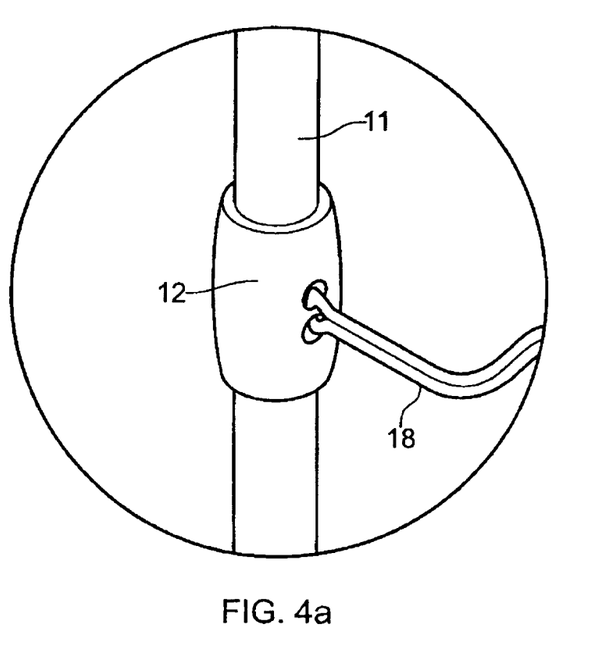
FIG. 4 is an exploded schematic view of the shuttle and suture of the present invention.
Figure 4B:
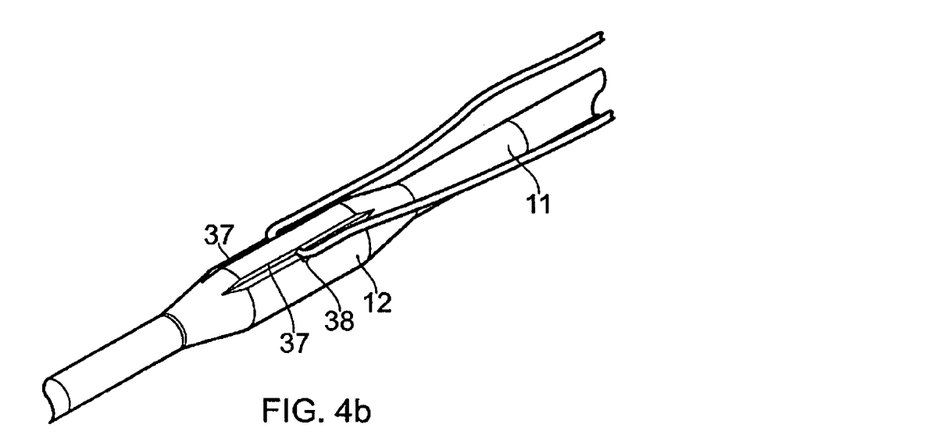
FIG. 4b is a schematic view of the shuttle of a further embodiment of the invention.
Figure 4C:
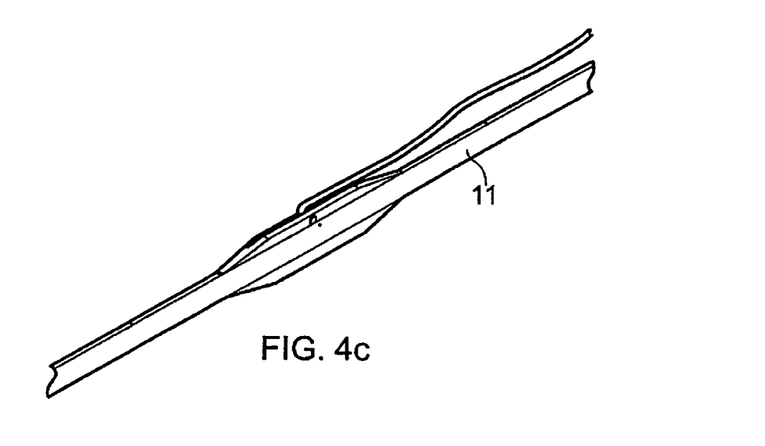
FIG. 4c is a sectional view of the embodiment of FIG. 4b.
Figure 4D:
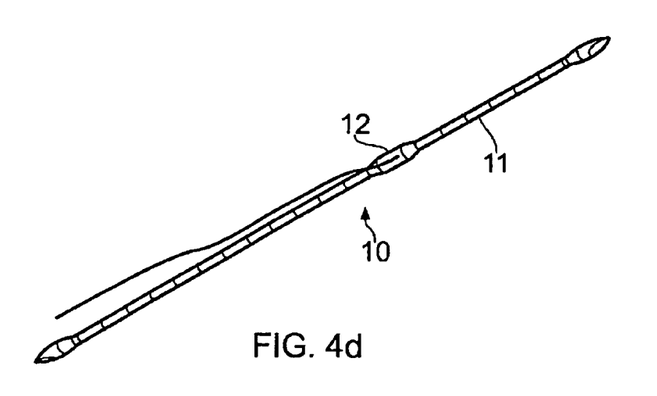
FIG. 4d is a view of the assembly of a further embodiment of the invention.

In the embodiment of the invention depicted in FIGS. 4b and 4c, rather than apertures, the shuttle has elongate longitudinal slits 37 to receive the suture. The suture may sit within a transverse slot 38 in the shuttle.

Figure 7:
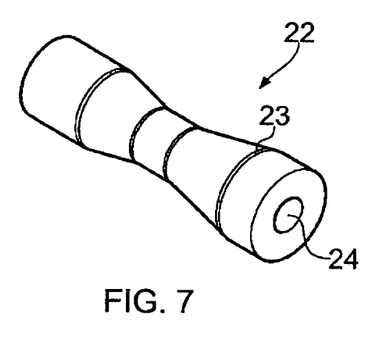
FIGS. 7, 7a and 7b depict an embodiment of the tethering member of the present invention.
Figure 7A:
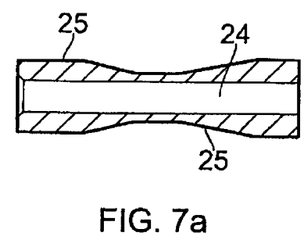
Figure 7B:
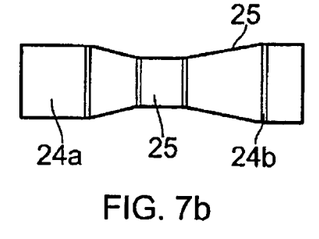

A leading length 19 of the suture is secured to a trailing length 21 of the suture by a tethering member 22. The tethering member 22 is spaced from said shuttle 12 and comprises a tubular body 23 having an inner lumen 24 to receive a length of suture 18. The inner lumen 24 is substantially straight whereas an outer surface 25, as depicted in FIG. 7a, defines a dumbbell structure with first and second end regions 24a and 24b having a greater thickness than a thinner central crimping region 25.

The tethering member is made from a malleable material which may be crimped at least at region 25 around the suture.

Figure 5:
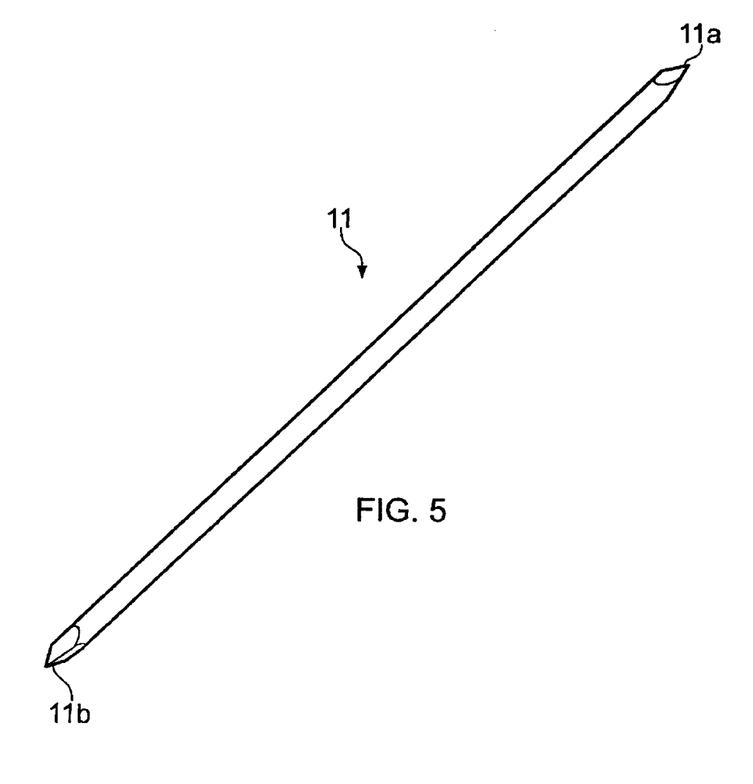
FIG. 5 is a side elevational view of an elongate shaft of an embodiment of the assembly of the present invention.
Figure 6:
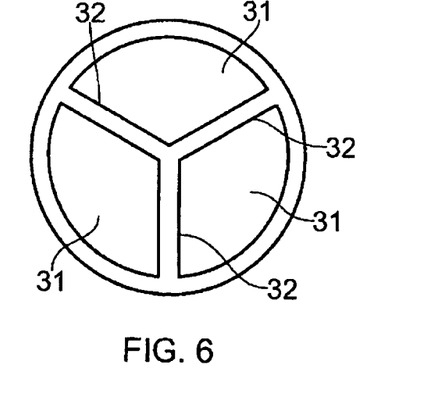
FIG. 6 is an end view of the elongate shaft depicted in FIG. 5.

The tissue piercing ends of the elongate shaft comprise trocar tips as depicted in FIG. 5. An end view of one of the tips depicted in FIG. 6 shows the three cutting planes 31 separating by cutting ridges 32.

Figure 9:
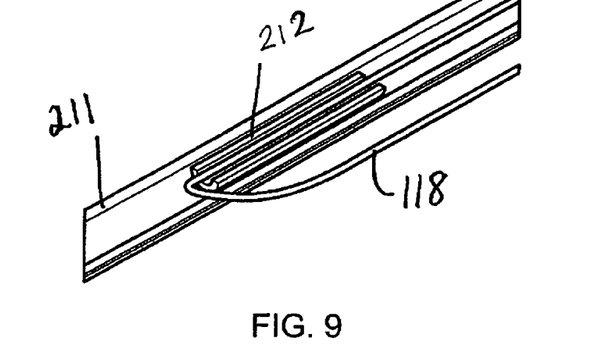
FIGS. 9 and 10 are sectional views of further embodiments of the invention.
Figure 10:
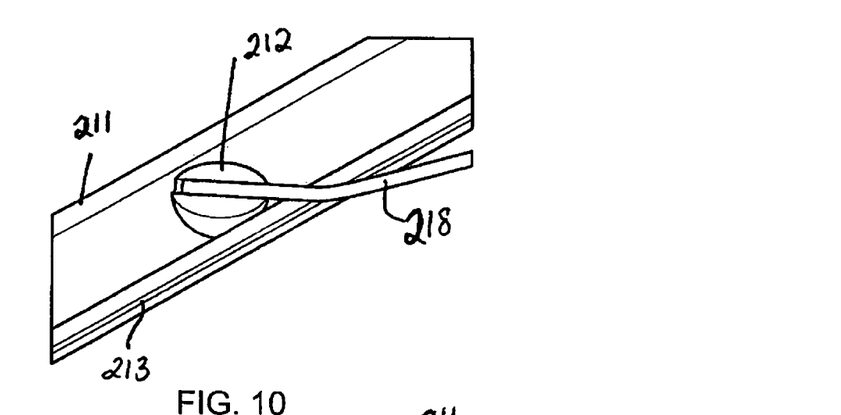
Figure 11:
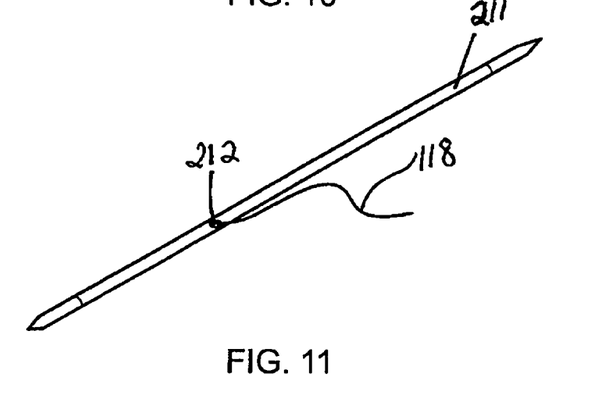
FIG. 11 is a side elevational view of the assembly of another embodiment of the invention.

Embodiments of an internal shuttle system are provided in FIGS. 9, 10 and 11. Internal shuttle 212 is housed within needle 211 to hold suture 218 therein. The internal shuttle is longitudinally moveable relative to the needle 211. Needle 211 has a longitudinal slot 213 along which suture 218 slides as the shuttle 212 moves longitudinally. Shuttle 212 in FIG. 10 is rotationally moveable within needle 211.

FIGS. 12a to 12d depict needle assembly 10 in use. First end 11a is introduced through the skin 100 at access site 101 and into the subcutaneous tissue. The needle assembly is passed subcutaneously and the first end 11a caused to exit the skin at first exit site 102, remote from the access site 101.

Figure 12A:
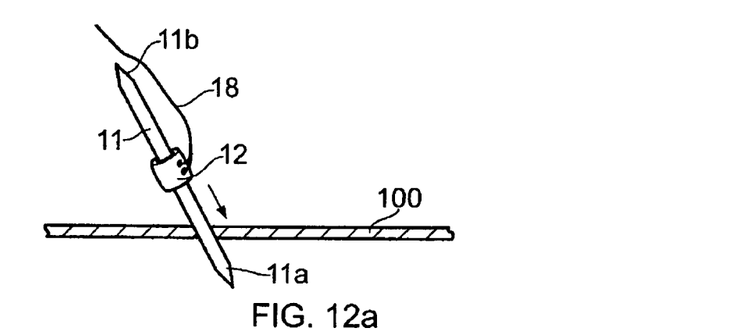
FIGS. 12a to 12d depict the assembly of the present invention in use.
Figure 12B:
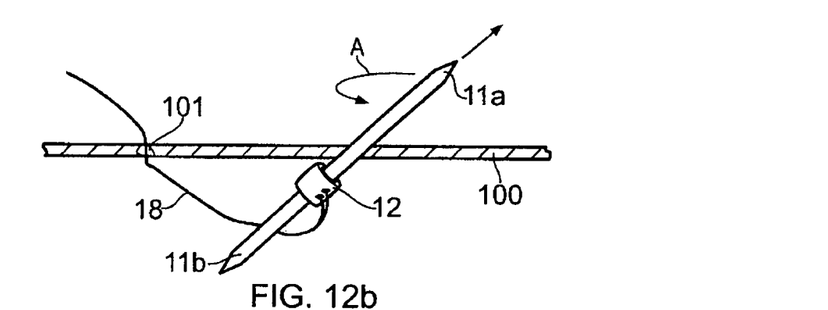
Figure 12C:
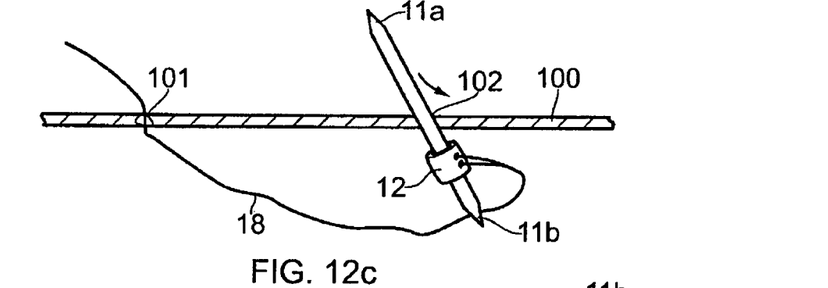
Figure 12D:
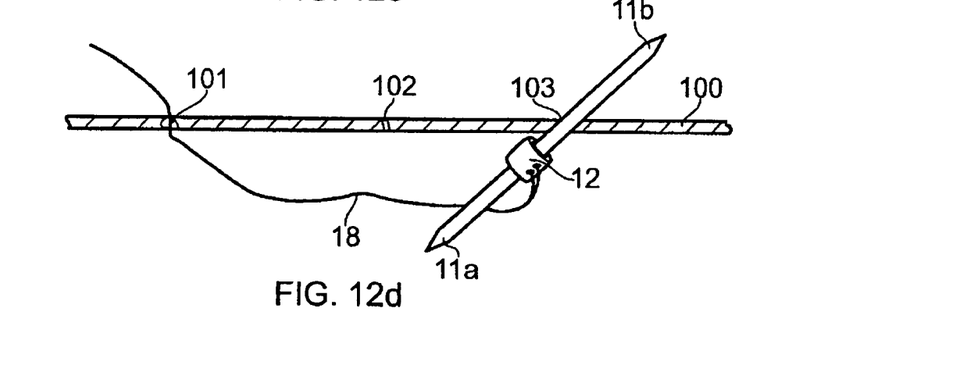

At this stage in the procedure, and as shown in FIG. 12b, the needle assembly is pivoted (depicted by arrow A) such that end 11b, which is positioned subcutaneously, travels beneath the skin before exiting at exit site 103. Exit site 103 is remote from both access site 101 and the first exit site 102.

These steps may be repeated as required. The advantage as depicted in these drawings is that the shuttle and the suture are retained subcutaneously. The shuttling of the shuttle 12 along the length of the shaft 11 enables the suture to travel along and be retained subcutaneously throughout the procedure. The retention of the suture by the shuttle provides a steady and smooth movement during the procedure and enables precision placement of the suture subcutaneously.

The invention claimed is:

1. A needle assembly comprising:
    an elongate shaft having a first tissue piercing end and a second tissue piercing end; and
    a shuttle member,
    said shuttle member comprising at least one suture securing means to secure a suture to the shuttle member and a substantially tubular body extending from a proximal end to a distal end and having an inner wall defining a lumen to receive at least part of the shaft, said lumen having a diameter which is greater than the diameter of the elongate shaft such that the shuttle member is freely moveable relative to said elongate shaft along a length of the elongate shaft between said first and second tissue piercing ends.

2. The needle assembly of claim 1 wherein the shuttle member is freely longitudinally moveable along said length of said elongate shaft.

3. The needle assembly of claim 1 wherein the shuttle member is freely rotationally moveable relative to the shaft.

4. The needle assembly of claim 1 wherein the elongate shaft comprises at least one stop means adjacent to the first tissue piercing end and at least one stop member adjacent to the second piercing end to prevent the shuttle member from travelling beyond the tissue piercing ends of the elongate shaft.

5. The needle assembly of claim 1 wherein an outer surface of the shuttle member is convexly curved relative to a longitudinal axis of the elongate member.

6. The needle assembly of claim 1 wherein the diameter of the shuttle member at its widest point is preferably less than or equal to the diameter of a widest region of the elongate shaft.

7. The needle assembly of claim 6 wherein the widest region of the elongate shaft comprises at least one of the tissue piercing ends.

8. The needle assembly of claim 1 wherein the shuttle member may further comprise a lubricious coating.

9. The needle assembly of claim 1 wherein the suture securing means of the shuttle comprises at least one aperture in the shuttle.

10. The needle assembly of claim 9 wherein the suture securing means comprises two apertures in the shuttle.

11. The needle assembly of claim 10 wherein the suture is looped through said apertures and secured thereto by a tethering member.

12. The needle assembly of claim 11 wherein the tethering member comprises a tubular body having an inner lumen to receive a length of suture and means to secure it there within.

13. The needle assembly of claim 1 for use in a cosmetic surgical procedure.

14. The needle assembly of claim 13 for use in a face lift or a breast lift procedure.

15. A method of subcutaneously positioning at least one suture in an individual, comprising:
    (a) providing a needle assembly comprising an elongate shaft having a first tissue piercing end and a second tissue piercing end; and
    a shuttle member comprising at least one suture securing means to secure a suture to the shuttle member and a substantially tubular body extending from a proximal end to a distal end and having an inner wall defining a lumen to receive at least part of the shaft, said lumen having a diameter which is greater than the diameter of the elongate shaft such that the shuttle member is freely moveable relative to said elongate shaft along a length of the elongate shaft between said first and second tissue piercing ends;
    (b) subcutaneously introducing the at least one suture by passing the first tissue piercing end of the elongate shaft into and under the skin of the individual;
    (c) moving said elongate shaft relative to the skin such that said first tissue piercing end exits the skin at first exit site, remote from the position at which it entered and wherein the second tissue piercing end, the shuttle member and at least a portion of the at least one suture is retained beneath the surface of the skin; and (d) passing the second tissue piercing end of the elongate shaft subcutaneously and causing it to exit the skin at a second exit site, remote from the first exit site; and wherein the first tissue piercing end and at least a portion of the at least one suture is retained beneath the surface of the skin.

16. The method of claim 15 including repeating steps (c) and (d) to further subcutaneously advance the at least one suture.

17. A needle assembly comprising:
an elongate shaft having a first tissue piercing end and a second tissue piercing end;
a shuttle member, said shuttle member comprising at least one suture securing means to secure a suture to the shuttle member and a substantially tubular body extending from a proximal end to a distal end and having an inner wall defining a lumen to receive at least part of the shaft, said lumen having a diameter which is greater than the diameter of the elongate shaft such that the shuttle member is freely moveable relative to said elongate shaft along a length of the elongate shaft between said first and second tissue piercing ends; and
a suture connected to the shuttle member.

18. The needle assembly of claim 17 wherein the suture is at least partially elastic.

19. The needle assembly of claim 18 wherein the entire suture is formed from an elastomeric material.

20. The needle assembly of claim 18 wherein the suture has an elastomeric core overlayed by an elastomeric sheath.

21. The needle assembly of claim 20 wherein the sheath is made from a material having less elasticity than the material of the core.

22. The needle assembly of claim 20 wherein the sheath is made from a material having greater elasticity than the material of the core.

23. The needle assembly of claim 18 wherein the suture has constant elasticity along its length.

24. The needle assembly of claim 18 wherein the suture has variable elasticity along its length.

25. The needle assembly of claim 17 wherein the entire suture is made from a biocompatible material.

26. The needle assembly of claim 17 wherein the suture thread includes one or more barbs along its length.

27. The needle assembly of claim 17 for use in a cosmetic surgical procedure.

* * * * *